(12) United States Patent
Olofsson et al.

(10) Patent No.: US 10,287,641 B2
(45) Date of Patent: May 14, 2019

(54) LACTOBACILLUS APINORUM AND LACTOBACILLUS MELLIFER FROM HONEYBEES IN MEDICAL, FOOD AND FEED APPLICATIONS

(71) Applicant: CONCELLAE AB, Gantofta (SE)

(72) Inventors: Tobias Olofsson, Råå (SE); Alejandra Vasquez, Råå (SE)

(73) Assignee: CONCELLAE AB, Gantofta (SE)

( * ) Notice: Subject to any disclaimer, the term of this patent is extended or adjusted under 35 U.S.C. 154(b) by 16 days.

(21) Appl. No.: 15/503,475

(22) PCT Filed: Aug. 13, 2015

(86) PCT No.: PCT/SE2015/050870
§ 371 (c)(1),
(2) Date: Feb. 13, 2017

(87) PCT Pub. No.: WO2016/024910
PCT Pub. Date: Feb. 18, 2016

(65) Prior Publication Data
US 2017/0226599 A1    Aug. 10, 2017

(30) Foreign Application Priority Data

Aug. 14, 2014 (SE) .................................... 1430114

(51) Int. Cl.
| | | |
|---|---|---|
| *A61K 39/02* | (2006.01) | |
| *A01N 63/00* | (2006.01) | |
| *A01N 65/00* | (2009.01) | |
| *C12R 1/225* | (2006.01) | |
| *C12G 3/025* | (2019.01) | |
| *C12N 1/20* | (2006.01) | |
| *C12P 5/00* | (2006.01) | |
| *C12P 7/26* | (2006.01) | |
| *C12P 7/64* | (2006.01) | |
| *C12C 12/00* | (2006.01) | |
| *A61K 35/747* | (2015.01) | |
| *A23L 33/135* | (2016.01) | |
| *A23K 20/10* | (2016.01) | |
| *A61K 35/00* | (2006.01) | |

(52) U.S. Cl.
CPC .............. *C12R 1/225* (2013.01); *A23K 20/10* (2016.05); *A23L 33/135* (2016.08); *A61K 35/747* (2013.01); *C12C 12/008* (2013.01); *C12G 3/025* (2013.01); *C12N 1/20* (2013.01); *C12P 5/005* (2013.01); *C12P 7/26* (2013.01); *C12P 7/6409* (2013.01); *A23V 2002/00* (2013.01); *A23Y 2220/00* (2013.01); *A61K 2035/11* (2013.01)

(58) Field of Classification Search
CPC ....................................................... A61K 39/09
USPC .................................. 424/93.1, 93.4, 93.45
See application file for complete search history.

(56) References Cited

FOREIGN PATENT DOCUMENTS

| WO | 03047642 A1 | 6/2003 |
| WO | 2004000339 A1 | 12/2003 |
| WO | 2008136730 A1 | 11/2008 |
| WO | 2012102668 A1 | 8/2012 |

OTHER PUBLICATIONS

Bitidningen, No. 10, Oct. 2013, pp. 11-13: Olofsson T, "Binas egna mjolksyrabakterier har blivit medicin for bin", link: http://www.biodlama.se/website1/1.0.1.0/2059/BT%2010-13.pdfm downloaded Feb. 10, 2015.
Olofsson TC et al., "*Lactobacillus apinorum* sp nov., *Lactobacillus mellifer* sp nov., *Lactobacillus mellis* sp nov., *Lactobacillus melliventris* sp nov., *Lactobacillus kimbladii* sp nov., *Lactobacillus helsingborgensis* sp nov and *Lactobacillus kullabergensis* sp nov., isolated from the honey stomach of the honeybee *Apis mellifera*", International Journal of Systematic and Evolutionary Microbiology, vol. 64, pp. 3109-3119, published online Jun. 18, 2014.
Youtube cut: "New medicine could save dwindling global bee population", published Sep. 27, 2013, link: https://www.youtube.com/watch?v=adAucmKvXBA&feature=youtube.
PCT International Search Report and Written Opinion dated Nov. 13, 2015 from corresponding Application No. PCT/SE2015/050870, 13 pages.
PCT International Preliminary Report on Patentability dated Feb. 14, 2017 from corresponding Application No. PCT/SE2015/050870, 9 pages.

*Primary Examiner* — Rodney P Swartz
(74) *Attorney, Agent, or Firm* — Dilworth IP, LLC

(57) ABSTRACT

The invention relates to new isolated *Lactobacillus* strains chosen from *Lactobacillus mellifer* Bin4N.sup.T (LMG P-28344) and *Lactobacillus apinorum* Fhon13N.sup.T (LMG P-28345), which have been isolated from honeybees or their processed food. The bacterial strains have unique properties such as production of benzene, free fatty acids and 2-heptanone, rendering them useful in many areas such as in food and beverage products, feed products and medical products.

3 Claims, 1 Drawing Sheet

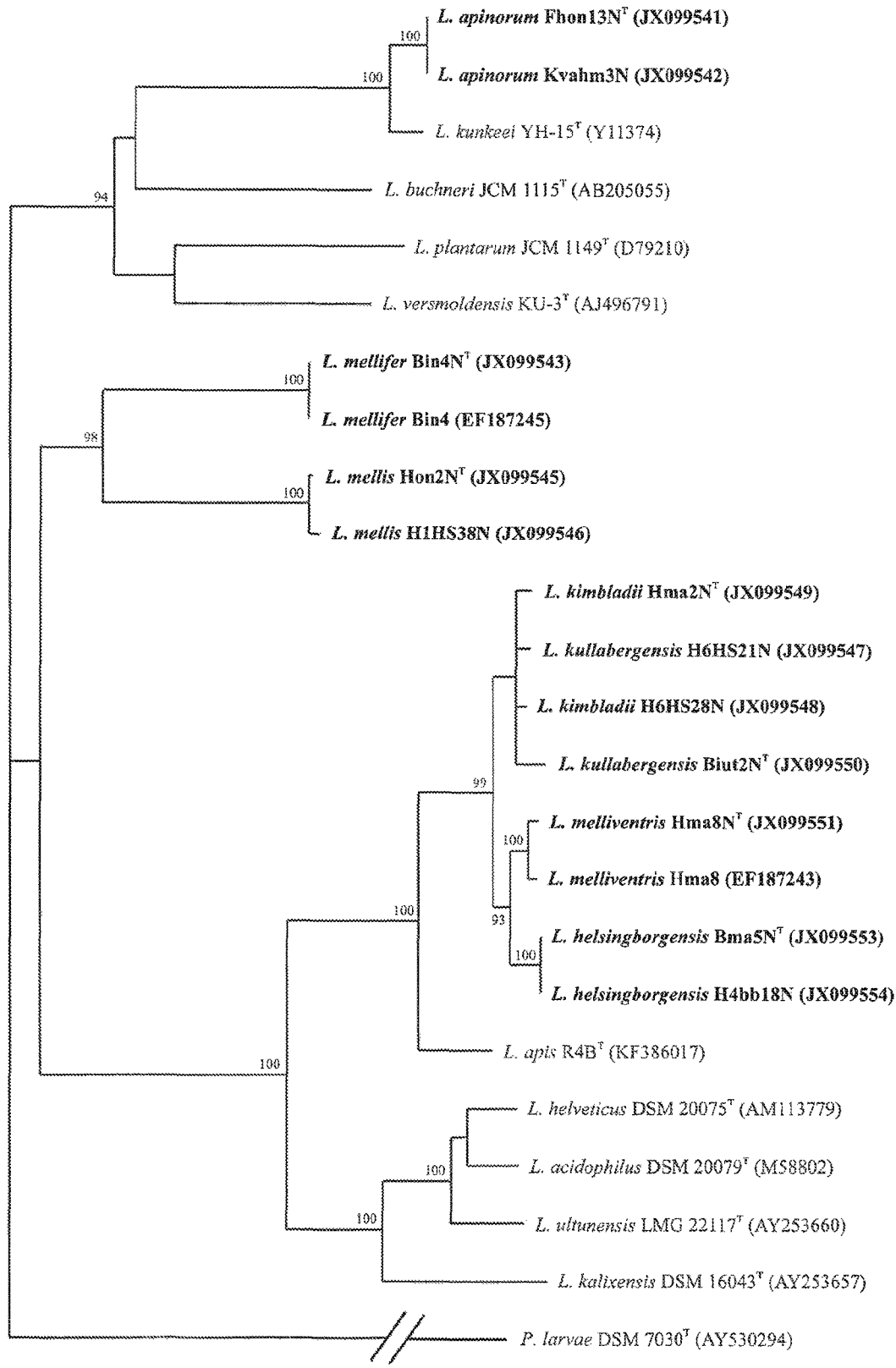

LACTOBACILLUS APINORUM AND LACTOBACILLUS MELLIFER FROM HONEYBEES IN MEDICAL, FOOD AND FEED APPLICATIONS

FIELD OF INVENTION

The invention relates to two newly isolated novel *Lactobacillus* type strains chosen from *Lactobacillus mellifer* Bin4N$^T$ (LMG P-28344) and *Lactobacillus apinorum* Fhon13N$^T$ (LMG P-28345), which have been isolated from honeybees and their processed food. These bacterial strains produce unique metabolites called benzene, Free fatty acids (3-OH FAs) and 2-heptanone, rendering them useful in many medically related products such as food, beverage, feed and wound care.

BACKGROUND OF INVENTION

Honey, the mysterious food used in medicine since ancient ages has puzzled people for centuries with it's healing effects on human wounds documented already by the Egyptians 2000 B.C.

Honey is produced by bees such as the honeybee *Apis mellifera*. The nectar bees collect from plants is a sweet liquid mostly composed of sucrose. By the time the bee returns to the hive, much of the sucrose is converted to glucose and fructose. Further, honey contains proteins, vitamins and minerals.

Presently, honey's therapeutic properties besides osmolarity and acidity, are explained by the hydrogen peroxide content as an action of peroxidase oxidase (White, et al. 1963 *Biochem Biophys Acta* 73, 57-70), the origin of the nectar by it's different flavonoid and phenolic acids content (Taormina, et al. 2001. *Int J Food Microbiol* 69(3), 217-225; Wandan, H. A. 1998. *Infection* 26(1), 26-31), and an unidentified component (Molan, P. C. 2001. World Wide Wounds (online); Available from URL: worldwidewounds.com). Despite scientific efforts performed during the last 30 years (Lusby, P. E., et al. 2005 *Arch Med Res* 36(5), 464-467; Molan, P. C. 2006. *Int J Low Extrem Wounds* 5(1), 40-54 *Int J Low Extrem Wounds* 5(2), 122; Mundo, M. A., et al. 2004 *Int J Food Microbiol* 1, 97(1), 1-8) the mystery regarding many of honey's modes of action still remains to be solved.

The antimicrobial properties possessed by honey render honey suitable for use in the dressing of wounds, where it assists in preventing infection, the debridement of necrotic tissue, the deodorising of malodorous wounds and the minimisation of scar formation. Honey containing wound and skin caring products are known through WO2004000339 and WO03047642.

For centuries, honey has been used as a folk medicine for the treatment of upper respiratory tract infections and wounds. Today, many of its antimicrobial characteristics have been recognized, however there are still unknown substances that contribute to this action.

It has been discovered that LAB symbionts from the honey stomach of honeybees are found in large concentrations in fresh honey as well as having a wide spectrum of antimicrobial activity against various bee pathogens and bacteria and yeasts from flowers. We hypothesise that many of the unknown healing and antimicrobial properties of honey are linked with these LAB symbionts.

Bee diseases are infections and parasitic conditions concerning enormous agriculture economics loss. Two of several hive intruders are the wax moth larvae (WML; *Galleria mellonella*) and the parasitic mite, *Varroa destructor*. The larvae of the wax moth is known to feed on the bees wax that otherwise is used by the bees for breeding of new bees and storage of their honey. *Varroa destructor* is known to be the worst honeybee parasite resulting in destruction of infected colonies in many countries. (Papachristoforou, A., et al. 2012. *PLoS ONE* 7(10): e47432. doi:10.1371/journal.pone.0047432) suggests that honeybees have got their own defense using their mandibles to bite these invaders that are too small to sting. The honeybees seem to secrete 2-heptanone (2-H) from their mandibular glands when they bite. 2-H is used as an anaesthetic in small arthropods, such as wax moth larva (WML) and *Varroa* mites, which are then paralysed or killed after a honeybee bite and thrown out of the hive.

The *Lactobacillus* genus is one of the most important groups within Lactic acid bacteria (LAB). LAB and especially *Lactobacillus* is considered as beneficial bacterial genus commonly found in healthy individuals (Coenye, T. and Vandamme, P. 2003. *Microbiology* 149, 3507-3517; Ouwehand, A. C., et al. 2002. *Antonie van Leeuwenhoek* 82, 279-289). They are commercially important for their use in dairy products and probiotics, causing beneficial effects in the host when administered (FAO/WHO 2002). Furthermore, *Lactobacillus* are well known for their preservative and flavor effects, e.g. in the food industry.

SUMMARY OF THE INVENTION

The invention relates to two new discovered *Lactobacillus* type strains (*Lactobacillus apinorum* and *Lactobacillus mellifer*), which have been isolated from honeybees and their processed food. These bacterial strains have unique properties, which render them useful in many areas such as in food, beverages, feed and medical products. Our studies show that these strains are not only producing common metabolites such as lactic and acetic acid but also other potent metabolites such as benzene, free fatty acids (3-0H FAs) and 2-heptanone (Olofsson, T. C. Butler E, Markowicz P, Lindholm C, Larsson L, Vásquez A. Lactic acid bacterial symbionts in honeybees—an unknown key to honey's antimicrobial and therapeutic activities. International Wound Journal 2016 October; 13(5):668-79). With a unique honey-related origin, the bacterial strains are well suited to be used in honey containing products. These products have unique health promoting and flavouring properties.

In one first aspect the invention relates to a product comprising at least one the two *Lactobacillus* strains (*Lactobacillus apinorum* and *Lactobacillus mellifer*), wherein said bacteria is obtainable by isolation from honeybees and/or their processed food (including honey, corbicular bee-pollen and bee bread).

In a second aspect the invention relates to a method for the manufacturing of a product comprising the steps of; isolating at least one bacterial strain from at least one honeybee or their processed food, growing said at least one bacterial strain, mixing said bacterial strain with a sugar source and obtaining a product.

In a third aspect the invention relates to new isolated and characterised bacterial type strains (Olofsson, T. C., et al. 2014. IJSEM, doi: 10.1099/ijs.0.059600-0) showing at least 95% 16S rRNA sequence similarity with the bacterial strain selected from the two type strains comprising *Lactobacillus mellifer* Bin4N$^T$ (LMG P-28344) and *Lactobacillus apinorum* Fhon13N$^T$ (LMG P-28345).

In a fourth aspect the invention relates to the use of the product described in the first aspect of the invention, a product obtained by the method described in the second aspect of the invention, or a bacterial strain as described in the third aspect of the invention, in a food product, feed product or medical product.

In a fifth aspect the invention relates to the isolated *Lactobacillus* strains wherein said bacteria is obtainable by isolation from honeybees or their processed food.

In a sixth aspect the invention relates to a food product comprising at least one of the isolated *Lactobacillus* strains wherein said bacteria is obtainable by isolation from honeybees or their processed food.

In a seventh aspect the invention relates to a feed product comprising at least one isolated *Lactobacillus* strain wherein said bacteria is obtainable by isolation from honeybees or their processed food.

In an eighth aspect the invention relates to a medical product comprising at least one isolated *Lactobacillus* strain wherein said bacteria is obtainable by isolation from honeybees or their processed food.

In a ninth aspect the invention relates to a beverage product comprising at least one isolated *Lactobacillus* strain wherein said bacteria is obtainable by isolation from honeybees or their processed food.

Further advantages and objects with the present invention will be described in more detail, inter alia with reference to the accompanying drawings.

BRIEF DESCRIPTION OF THE DRAWINGS

FIG. 1 illustrates a phylogenetic tree including the bacterial strains according to the invention. The phylogenetic tree derived from 16S rRNA gene sequence analyses, showing the relationship of the novel type strains *Lactobacillus apinorum* Fhon13N$^T$ and *Lactobacillus mellifer* Bin4N$^T$ to members of the *L. buchneri* and *L. delbrueckii* subgroups of lactobacilli. The sequence of *Paenibacillus larvae* served as outgroup. Approximately 1450 nt from each sequence were used for the alignment. Bar: 0.01 substitutions per nucleotide position. Numbers indicate bootstrap values for branch points. 16S rRNA gene sequences have been deposited in GenBank (in parenthesis).

DETAILED DESCRIPTION OF THE INVENTION

Definitions

In the context of the present application and invention, the following definitions apply:

The term "honey" means the sweet, viscous liquid produced by bees from the nectar of flowers.

The term "sugar source" means in general a sweet soluble disaccharide or small oligosaccharide carbohydrate. Examples of sugar sources are honey, sugar, glucose, fructose, sucrose and maltose.

The term "CFU" means colony-forming unit.

The term "lactic acid bacteria, LAB" relates to bacteria producing lactic acid, such as bacteria belonging to the genera *Lactobacillus, Lactococcus* and *Bifidobacterium*.

The term "probiotic microorganism" refers to a microorganism that form at least a part of the transient or endogenous flora and thereby exhibit a beneficial prophylactic and/or therapeutic effect on the host organism.

The term "molecular marker" is intended to mean a stretch of a nucleotide sequence, which may be used to identify a bacterial strain or related bacterial strains. The molecular marker may be used in hybridisation assays as well as in amplification assays such as in Polymerase Chain Reaction (PCR).

The term "excipient" means any non-active ingredient added to a product or composition.

In this specification, unless otherwise specified, "a" or "an" means "one or more".

Honeybee Specific Bacterial Strains

The invention relates to a product comprising at least one of the isolated *Lactobacillus* strains chosen from *Lactobacillus mellifer* Bin4N$^T$ (LMG P-28344) and *Lactobacillus apinorum* Fhon13N$^T$ (LMG P-28345), wherein said bacterial strain is obtainable by isolation from a honeybee or their processed food. The invented product may further comprise a salt or sugar source as defined above, such as being selected from the group comprising honey, sugar, fructose, sucrose, maltose and glucose. One specific example being honey.

Accordingly, the invented product may comprise at least one bacterial strain or mixture of strains selected from the group comprising *Lactobacillus mellifer* Bin4N$^T$ (LMG P-28344) and *Lactobacillus apinorum* Fhon13N$^T$ (LMG P-28345). The invention also relates to the isolated bacterial strains as such. The above identified and isolated bacterial type strains have been isolated from honeybees and their processed food. The unique bacterial source has resulted in isolated bacterial strains with novel and beneficial properties. The isolated bacterial strains according to the invention are not harmful to humans.

The bacterial strains *Lactobacillus mellifer* Bin4N$^T$ (LMG P-28344) and *Lactobacillus apinorum* Fhon13N$^T$ (LMG P-28345) were deposited on Jun. 6th 2014 at the BCCM/LMG Bacteria Collection in Belgium in accordance with international deposits under the Budapest Treaty.

In an embodiment of the invention, the above mentioned strains *Lactobacillus mellifer* Bin4N$^T$ (LMG P-28344) and *Lactobacillus apinorum* Fhon13N$^T$ (LMG P-28345) are combined with the previously known strains *Lactobacillus* strain Biut2 (LMG P-24094), *Lactobacillus* strain Hma2 (LMG P-24093), *Lactobacillus* strain Hma8 (LMG P-24092), *Lactobacillus* strain Bma5 (LMG P-24090), *Lactobacillus* strain Hon2 (LMG P-24091) said strains being deposited at BCCM/LMG Bacteria Collection in Belgium on 3 Apr. 2007, *Bifidobacterium* strain Bin7 (LMG P-23986), *Bifidobacterium* strain Hma3 (LMG P-23983), *Bifidobacterium* strain Bin2 (LMG P-23984), *Bifidobacterium* strain Bma6 (LMG P-23985) and *Lactobacillus kunkeei* Fhon2 (LMG P-23987), said strains being deposited at BCCM/LMG Bacteria Collection in Belgium on 15 Jan. 2007 and Hma11 (LMG P-24612) deposited on Apr. 28, 2008 at BCCM/LMG Bacteria Collection in Belgium. The combination of the 13 strains may be done in any of the products as mentioned herein, i.e. in a food, beverage, feed, functional food or medical food.

FIG. 1 discloses a phylogenetic tree derived from 16S rRNA gene sequence analyses, showing the relationship of the novel type strains *Lactobacillus apinorum* Fhon13N$^T$ and *Lactobacillus mellifer* BIN4N$^T$ to members of the *L. buchneri* and *L. delbrueckii* subgroups of lactobacilli. The sequence of *Paenibacillus larvae* served as outgroup. Approximately 1450 nt from each sequence were used for the alignment. Bar: 0.01 substitutions per nucleotide position. Numbers indicate bootstrap values for branch points. 16S rRNA gene sequences have been deposited in GenBank (in parenthesis).

The isolated bacterial type strains may be identified by a molecular marker. The molecular marker may be derived from nucleotide sequences of the said strains. The length of the molecular marker being dependent on the assay to be used for the identification of the bacterial strain and is obvious for a person skilled in the art.

Further, the invention relates to bacterial strains showing at least 95%, 97% or even 100% homology to the 16S rRNA sequences selected from the group of the two type strains *Lactobacillus apinorum* and *Lactobacillus mellifer*.

The bacterial strains have been identified to be honeybee specific, found in honeybees or in their processed food.

The bacterial strains are producers of Benzene, Para Dichloro Benzene (PDB), 2-Heptanone and Free fatty acids (3-OH). All of these molecules were shown to be present in honey or in the beehive atmosphere as volatiles (Tables 3-5) and thus may attribute to honey's antibacterial properties, taste and quality and to improve honeybee health by an inhibitory effect against hive intruders such as *Varroa destructor, Nosema apis/cerranae*, wasps etc. These inhibitors produced by the bacterial strains display an effective inhibitory potential against other species of bacteria and yeasts, pathogens in human wounds (Table 2). The bacterial strains (*Lactobacillus apinorum* and *Lactobacillus mellifer*) are very potent inhibitors of wound pathogens resistant to antibiotics. The bacterial strains are also very potent inhibitors of yeasts belonging to the genus *Saccharomyces* that are commonly found in honey. Because of honey's extreme sensitivity to yeast, it can be expected to ferment even with only 1 spore per gram of honey if its water content is above about 18%. The preservation of honey by the two bacterial strains described is thus crucial for the long-term storage of honey but also in mead production. The preservation capabilities of the bacterial strains render them useful in many preservation applications, not only for the preservation of honey but also for the preservation of food and beverages in general.

The invention also relates to isolated, pure cultures of the bacterial strains. Such pure cultures may be provided as colonies on agar plates, as liquid cell suspension or as a frozen, spray-dried or freeze-dried preparation. The cultures may be used alone or in combination in any application, such as in a food or beverage product, feed product or medical product. Further, the culture may contain and may be used to produce metabolites, antibacterial compounds and/or bacteriocins, which can be used in a variety of products or compositions, such as exemplified above.

Further, the products or compositions according to the invention can comprise both of the two different strains of bacteria. By combining the two strains the effects of the bacteria will be utilized in a synergistic manner so that more species of pathogens will be combated. Further, the efficiency of the products will be enhanced since many different inhibitory substances will be produced.

The product may contain a salt source (NaCl) or sugar source, wherein the sugar source is selected from the group comprising honey, sugar, fructose, sucrose, dextrine, maltose or glucose. By producing a product containing the bacterial strains according to the invention in combination with honey the bacterial strains will perform their functions in a synergistic manner with the honey. Therefore, it may be desirable to combine the effects of honey with added bacterial strains according to the invention.

The products according to the invention can be produced by a method of manufacturing comprising the steps of; isolating at least one bacterial strain from a honeybee or honeybee processed food, growing said at least one bacterial strain, mixing said bacterial strain with a sugar source and obtaining a product. The sugar source may be selected from the group comprising honey, sugar, fructose, sucrose, dextrine, maltose or glucose.

Food or Beverage Product

A product or composition of the invention comprises at least one of the strains and may be prepared in the form of a food or beverage product by using suitable food or beverage components or nutrients. The food or beverage can be used as a probiotic, prebiotic or synbiotic composition or product.

By the addition of one or both the bacterial strains new and improved products are obtained. These products may contain live, freeze-dried or killed bacteria. Further the product may contain metabolites produced by the bacteria. A product containing freeze-dried bacterial strains can be activated by the addition of water.

By using the bacterial strains according to the invention a highly natural product may be produced. By combining the two bacterial strains of the invention the effects of the bacteria will be utilized in a synergistic manner. In this way a standardized occurring mix of bacterial strains will be obtained. The use of a mixture of bacterial strains also increases the chance of knocking out various undesirable pathogens.

A product may comprise a sugar source selected from the group comprising honey or for example sugar, fructose, sucrose, maltose and glucose. By producing a product or composition containing the bacterial strains according to the invention in combination with a sugar source such as honey the bacterial strains will perform their functions in a synergistic manner with the sugar source. It is desirable to combine the effects of honey with added bacterial strains according to the invention. Honey and bacteria containing beverages such as a honey water beverage can be prepared. The honey water beverage can be prepared by mixing water, honey, bacterial strains according to the invention and a fruit juice such as lemon juice, lime juice, orange juice or apple juice. The concentration of bacterial strains in the beverage may be from about $10^1$ to $10^{14}$ CFU/g product, such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product. This concentration of bacterial strains can also be used in a beverage product without added honey. A concentration about $10^5$-$10^8$ CFU/g product may be used in a product mimicking the naturally occurring concentration of bacterial strains in fresh honey. The honey water beverage may also be prepared in form of a concentrate, with less or no water content and with freeze dried bacterial strains and juice as mentioned before.

A honey food product may further be used as an ingredient for the production of other food products.

It is an aim of the invention to make use of food or beverages containing bacterial strains more easily accessible to, frequent and usual with any consumers, for the purpose of increasing, supplementing and balancing the intestinal flora, which will bring about advantages in terms of everyday health and sports activity.

It is a further aim of the present invention to make available on the market, functional food or beverages containing mixtures of bacterial strains, which are capable of reaching the intestines in a live or viable form and also their metabolites, settling in the bacterial flora, influencing or growing, thereby performing important beneficial actions for the human health. The bacterial strains reaching the intestine may also be in a non live state, then performing a beneficial action via their produced metabolites and proteins. The food or beverage may be used for the prevention and/or treatment of gastrointestinal diseases.

Examples of beverages are milk products, juice products, wine, vinegar, Swedish Glögg, beer, mead, soda, lemonade and cider products. A beverage comprising one or more bacterial strains according to the invention and the addition of honey may be in form of honey water against cold or sour throat (upper respiratory infections), as recovery for athletes, stressed persons or for recovery for immune suppressive hospital patients. A beverage may be characterized by its special constitution with minerals and other substances that give the desired natural effect as in fresh honey.

The beverage or food with added bacterial strains according to the invention will benefit from the conserving effect of the bacterial strains. Yeast fermentation will be strongly inhibited. Further, the bacterial strains can be used in for example wine- or mead production for lowering the normal yeast activity in the fermentation. The bacteria will sustain as a naturally originating health benefiting bacteria in the product.

The food or beverage may also contain additives such as way of examples vitamins, minerals, antioxidants, phenols, fibres, oligosaccharides, fructooligosaccharides or innulin.

Examples of food products are meat products, dairy products, fruit products, fish products, bakery products or vegetable products. A food product may contain a sugar source such as honey. The food product can be fresh honey or mature honey with added bacteria according to the invention. The honey food product can be prepared by adding the bacterial strains according to the invention or a mixture of bacterial strains according to the invention to the honey or other products. The concentration of bacterial strains can be suitably selected so as to achieve a concentration from about $10^1$ to $10^{14}$ CFU/g product such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product.

The bacterial strains according to the invention can also be used as starter cultures for the fermentation of food and beverages. Examples of food and beverages are bred, milk, buttermilk, cacao, vanilla, coffee, cheese, green cheese, cucumbers, feed additives, fermented fish products, fermented milks, olive oil, sauerkraut, sausages, yoghurt, wine, beer, cider, mead and honey.

Medical Product

The bacterial strains according to the invention are valuable for preventing or treating infections as they inhibit growth of pathogenic microorganisms in humans and animals. The strains and the products containing them may be transferred to the human or animal skin in forms such as ointments, creams, sprays, gels and liquid solutions. The bacterial strains may also be included in products such as dressings, dermal patches, gels, or bandages containing effective amounts of bacterial strains in various parts of the products so as to achieve the desired result of preventing or inhibiting infections. The products may be used for the treatment of wounds, sores, burns, scars, bed sores, diabetic lesions, acne, eczema, dermatitis, cancer, catarrh, rash, yeast infections, toxic shock syndrome, fungal infections, viral infections and ulcers.

The product may be used in the treatment of bacterial, viral, yeast or fungal infections. Viral infections of interest may be *herpes* virus infections including *Herpes labialis*. Bacterial infections to be combated by the bacterial strains according to the invention may be infections by species selected from the group comprising *Staphylococcus* species, *Streptococcus* species, *Bacillus* species, *Enterococcus* species, *Pseudomonas* species, *Escherichia coli*, *Aspergillus* species, *Clostridium* species, *Candida* species, *Klebsiella* species, *Aerobacter* species, *Proteus* species, *Acremonium* species, *Helicobacter* species, *Salmonella* species, *Campylobacter* species and *Microsporum* species.

The medical products may include the bacterial strains in combination with a sugar source such as honey. The product will then benefit from known effects of honey in combination with the effects of the bacterial strains. The product may include varying percentages by weight of creamed or crystallised honey, spray dried, freeze-dried; air dried honey and/or liquid honey. The honey may be fresh or mature.

The medical product may include the metabolites and/or bacteriocins and/or proteins produced by the bacterial strains according to the invention. This product may additionally be sterilised in a known manner in order to achieve a sterile product without any viable bacteria. The product will benefit from the metabolites previously produced by the bacterial strains.

The active ingredients i.e. live or dead bacterial strains and bacteriocins and/or metabolites may comprise about 0.1% to about 100%, such as 1% to 70%, such as 5% to 50% by weight of the final product. A typical product will contain in a one gram dosage formulation a concentration of from $10^1$ to $10^{14}$ CFU, such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU of viable or killed bacteria.

The medical product may include both of the bacterial strains of the invention or metabolites produced from the bacterial strains according to the invention. A mixture of the bacterial strains or metabolites or proteins from them may be beneficial regarding the pathogen inhibition efficiency.

The medical product may also include the bacterial strains in a chewing gum. This product can be used in the treatment of for instance gingivitis and plaque. Ingredients of a chewing gum product can be one or more of honey, bees' wax, gum and other ingredients known in the art.

Optional ingredients in the medical product include pharmaceuticals such as antibiotics, fungicides and other antibacterial agents, vitamins, buffering agents, coloring agents, minerals, flavorings, fragrances, gelling agents or other chemical compounds such as antioxidants or calcium.

The medical product may include a base material in the form of a film, woven dressing, layered sheet dressing, patch, strap, rope configuration or wrap. Options for the base material include agar gel film, alginate dressing, hydrocolloid, foam dressing, and so forth. Further the product may comprise the bacterial strains according to the invention along with pharmaceutically or physiologically acceptable carriers, excipients and/or diluents. Carriers for dry formulations may be trehalose, malto-dextrin, rice flour, microcrystalline cellulose, magnesium stearate, inositol, and others. Liquid or gel-based carriers can be water, salt solutions, alcohols and the like. A medical product may then be formed by applying the bacterial strains to an absorbent or the like.

The medical product may be in form of a pharmaceutical product using pharmaceutically acceptable carriers together with the bacteria according to the invention. Examples of pharmaceutically acceptable carriers include various diluents and excipients such as fillers, extenders, binders, humectants, disintegrators, surfactants, lubricants and other carriers known in the art. The dosage may be in form of a pill, tablet, powder, solution, suspension, emulsion or granules. Tablets may be coated with a standard coating material. The amount of bacterial strains in the pharmaceutical product may be selected from about $10^5$ to $10^{14}$ CFU/dosage of the product, such as $10^5$, $10^6$, $10^7$, $10^8$, $10^9$, $10^{10}$, $10^{11}$, $10^{12}$ or $10^{13}$ CFU. The medical product may be used for the prevention and/or treatment of gastrointestinal diseases.

Feed Product

The bacterial strains according to the invention may be valuable in feed products for bee and bee larvae. These products may be in form of a probiotic feed used to strengthen or re-establishing the microbial flora within the bee or bee larvae and re-establishing the inhibitory atmosphere inside the beehive. The used bacterial strains are naturally occurring bacterial strains in honeybees or their processed food. Thus, the bacterial strains according to the invention will not knock out any naturally occurring bee specific lactic acid bacterial strains within the honey bee or their processed food. The usage of other beneficial bacterial strains not originating from the honeybee or their processed food, in similar products, could alter the natural bacterial flora of the honeybee in a negative matter. Therefore this type of feed product according to the invention will be particularly interesting.

The feed product may include one or both of the bacterial strains. A mixture of the strains may be beneficial regarding the treatment efficiency.

The concentration of bacterial strains can be suitably selected so as to achieve a concentration from about $10^1$ to $10^{14}$ CFU/g product such as $10^1$, $10^2$, $10^3$, $10^4$, $10^5$, $10^6$, $10^7$, $10^8$, $10^9$, $10^{10}$, $10^{11}$, $10^{12}$ or $10^{13}$ CFU/g product.

The feed product may be used for the protection of honeybee or honeybee larvae from pathogenic bacteria, virus, fungus or parasites. Organisms commonly leading to lethal infections and to be combated by the product are *Varroa destructor* and the wax moth larvae (WML; *Galleria mellonella*).

The bacterial strain or bacterial strain mixture may be administered to the honeybees or honeybee larvae as a powder, solution or as a solid. A powder may be in a freeze-dried, spray dried or air-dried form. A powder is simple to handle, transport, store and has a more expanded date of expiration. The powder or solution may be sprinkled or sprayed over the honeybees or larvae. Spraying or sprinkling a powder or solution directly over the honeybee nest may also accomplish effective administration.

The feed product may also contain a sugar source. The sugar source can be honey, sugar, sucrose, glucose, fructose, dextrine, maltose or other forms of sugar. The honeybee or honeybee larvae may use the sugar source as an energy source. By using honey in the sugar solution several advantages are gained. Firstly, the bees will be more eager to use a honey containing solution than a plain sucrose containing solution. Secondly, honey contains additional beneficial components such as minerals, vitamins and proteins.

When using the bacterial strains according to the invention a honeybee feed containing them will benefit from the bacteria and yeast inhibition properties of the bacteriocins, proteins and metabolites. Consequently, the sugar solution will not ferment, as is normally the case for sugar solutions.

The feed product may also contain pollen or soybean powder, both important food sources for honeybees and honeybee larvae during autumn, winter and spring. The feed product may also contain other additives such as vitamins, minerals, fat, carbohydrates and proteins.

The administration of the bacterial strains is particularly important in autumn or winter when the honeybee societies are week and resting. The bacterial strains will also function as a preservative of the honey or sugar present in the society. In the period of autumn, winter and early spring when no nectar is available, the bees and bee larvae are particularly vulnerable to bacterial, viral, fungal and parasitic infections. By the administration of bacterial strains according to the invention to the honeybees and honeybee larvae, the bacteria will grow out to a viable state when they reach the honeybee honey-producing tract, which is their original natural environment. Thereby, the bee and larvae will have acquired a more efficient protection against honeybee and larvae pathogens.

Following examples are intended to illustrate, but not to limit, the invention in any manner, shape, or form, either explicitly or implicitly.

EXAMPLES

Example 1—Natural Benzene Derivatives Against Wax Moth

When chemicals are used to fight of different bee diseases in the hive it is always a fine balance between using sufficient to kill off the pathogen/parasite and not killing off the bees themselves. A treatment, which was in common use and advised in older books, killing off the wax moth larvae, was the use of para dichlorobenzene (PDB) crystals. This moth deterrent was extremely effective but the chemical can accumulate in the wax and possibly damage bee larvae and contaminate honey. Therefore it is no longer acceptable to use it (Leaflet from The British Beekeepers Association—July 2012). We wanted to find out if the two *Lactobacillus* strains originating in honeybees produce any kind of benzene derivatives and in natural amounts helping the bees fighting of the wax moth larvae or preventing attack from it.

TABLE 1

Bioactive substances produced by each of the two strains from honeybees (*A. mellifera*). The table depicts volatiles (benzene and ethylbenzene). The depicted amounts refer to microgram per sample.

| Strain | Benzene | Ethylbenzene |
| --- | --- | --- |
| *Lactobacillus apinorum* Fhon13 $N^T$ | 0.0018 | 0.031 |
| *Lactobacillus mellifer* Bin4$N^T$ | 0.074 | 0.017 |
| Average in measuered hives | 0.0050 | 0.0010 |

Three different instruments from Swedish Environmental Research Institute in Gothenburg (IVL) were used for the measurement of volatile compounds (Benzene is a volatile) in air when the strains were cultivated in the laboratory and for measurements within beehives. The two strains were cultivated in the laboratory, in individual tubes with either sterilized honey and bee pollen or MRS broth (Oxoid), and volatiles in the atmosphere of the tubes were measured. Meters for Benzene, Toluene, n-Octane, Ethylbenzene, m+p-xylene, o-xylene and n-nonane were applied for measurements in tubes and hives. Both Benzene and Ethylbenzene were produced by the two strains (*Lactobacillus apinorum* and *Lactobacillus mellifer*) in the laboratory and also detected in the atmosphere of all the beehives included in the trial (Table 1).

Example 2—Human Wound Pathogens

The inhibitory effect against severe multidrug-resistant pathogens from chronic wound infections was tested (Olofsson, T. C. Butler È, Markowicz P, Lindholm C, Larsson L, Vásquez A. Lactic acid bacterial symbionts in honeybees—an unknown key to honey's antimicrobial and therapeutic activities. International Wound Journal 2016 October; 13(5): 668-79). Used pathogens (Table 2) were cultivated in Nutrient broth (Oxoid) at 37° C. during 24 hours prior to test in the antagonism assays.

Dual Culture Overlay Assay Antimicrobial activity was measured by using dual culture overlay assay. The *Lacto*-

*bacillus apinorum* and *Lactobacillus mellifer* strains (Table 2) were put into a filter disk and placed onto supplemented MRS agar plates followed by overnight incubation at 35° C.

Table 2

TABLE 2

The diameters of the inhibition zones are displayed in millimetres. Antibiotics commonly used against the same pathogens are depicted as controls.
Table 2. Dual culture overlay assays with LAB strains of bee origin against clinical isolates of pathogenic wound bacteria and yeast. The diameters of the inhibition zones are displayed in millimetres. Antibiotics commonly used against the same pathogens are depicted as controls.

|  | Serratia narcescens NJ19 5c | Klebsiella aerogenes Clmp R | Citrobacter Freundii CR01 5A | Staphylococcus areus 74022 PR | Pseudomonas aeruginosa LE08 | Enterobacter cloacae JSB 5B |
|---|---|---|---|---|---|---|
| *Lactobacillus apinorum* Fhon13 $N^T$ | $^S8$ | *10 | *18 | $^S20$ | 0 | 0 |
| *Lactobacillus mellifer* Bin4$N^T$ | $^S39$ | $^S26$ | *32 | $^B22$ | $^S29$ | $^S29$ |

|  | MRSA clinical isolate 18 | Escherischia coli V517 | Candida albicans | Enterococcus faecalis E12 VRE | Acinetobacter A23 Z32524 |
|---|---|---|---|---|---|
| *Lactobacillus apinorum* Fhon13 $N^T$ | 18 | *12 | 0 | $^S14$ | 13 |
| *Lactobacillus mellifer* Bin4$N^T$ | $^B32$ | $^B30$ | *20 | 21 | $^S40$ |

| Antibiotics | V | Cx | Cl | F | Cn | C | Cn | V | F | A | A | C |
|---|---|---|---|---|---|---|---|---|---|---|---|---|
|  | 9 | 28 | $^S19$ | $^B29$ | 19 | *31 | $^S21$ | 23 | $^S29$ | 0 | 19 | 0 |

Wound pathogens cultures were mixed with a 10 ml soft Nutrient agar (0.8%), holding a temperature of 42° C. Each mixture of soft agar was poured as an over layer on top of MRS plates with the overnight cultivated LAB. The plates were incubated at 37° C. for 24 hours. All the tests were performed in triplicate. Zone diameters were measured from centre of disk to zone edge.
$^S$(Sharp edge of inhibition zone),
$^B$(Blur edge of inhibition zone),
*(Sporadic growth all the way in through the zone),
ND (Not determined),
$^G$(Repeated twice).
Used antibiotics: V (Vancomycin, 30 µg), F (Fusidic acid, 10 µg), Cx (Cefuroxime sodium, 30 µg), Cl (Chloramphenicol 30 µg), Cn (Gentamicin, 10 µg), A (Ampicilin, 10 µg), C (Ciprofloxacin, 5 µg).

The Overlay assays (Table 2) display that all tested pathogens from clinical human wounds were inhibited by antimicrobial compounds diffusing from each of the two LAB strains originating from honeybees (*A. mellifera*). The results show that they together inhibit all tested pathogens but also that *Lactobacillus mellifer* Bin4$N^T$ is able to inhibit all tested pathogens on its own. Important to note is that the two *Lactobacillus* strains display varying inhibitory effects against the individual pathogens tested which is depicted in table 3. For example, normally a sharp edged inhibition zone displays a more efficient inhibition than when it is blur. Therefore, when acting together the two strains inhibit the pathogens in a more efficient way. Table 2:

Overall the inhibitory effects of the two strains are better or similar to the effects of tested antibiotics relevant for each pathogenic strain.

Example 3—Free Fatty Acids 3-OH

Certain species within LAB may produce bioactive compounds such as free fatty acids (3-OH) that are inhibitory against pathogens. We tested if either of the two strains produce 3-OH and if it is possible to find these bacterial metabolites in honey produced by honeybees using these strains (Olofsson, T. C., Butler È, Markowicz P, Lindholm C, Larsson L, Vásquez A. Lactic acid bacterial symbionts in honeybees—an unknown key to honey's antimicrobial and therapeutic activities. International Wound Journal 2016 October; 13(5):668-79).

The LAB species were grown in 5 ml supplemented MRS and 5 ml Pollen media until they reached their early stationary phase, after approx. 24 hours of incubation at 35° C. (13). Three milliliters of the supernatant was filtered through a 0.20 µm filter (Sarstedt). The filtered supernatants were freeze-dried during 18 hours at −20° C. before the GC-MS analysis.

The freeze-dried bacterial supernatants, and both stored and fresh harvested honey samples (200 mg), were analyzed for 3-OH FAs. In brief, the preparations were heated in acid methanol, extracted with heptane, and purified using silica gel columns. The hydroxy fatty acids, in the polar lipid fraction, were then subjected to derivatization to form trimethylsilyl derivatives, and analyzed by GC-MS/MS using an ion-trap instrument. Some of the samples were also analyzed in scan mode using a quadrupole GC-MS instrument. The 3-hydroxy fatty acids monitored were 3-OH C 10:0-3-OH C 22:0.

Free fatty acids (3-OH FAs) were identified from one of these *Lactobacillus* type strains studied, *Lactobacillus apinorum* Fhon13$N^T$; these were C 10:0, C 12:0, C 14:0 and C 16:0 (Table 3). Only results from Pollen media are shown as the results from bacteria incubated in MRS contained 3-OH FAs in the blank. In addition to the monitored 3-OH FAs compounds type strain *Lactobacillus apinorum* Fhon13$N^T$ produces a compound eluting just before 3-OH C 16:0. Its mass spectrum, as recorded by quadrupole GC-MS, revealed a peak m/z 341 strongly indicating that the compound represents 3-OH C16:1 (data not shown). Furthermore, most of the detected free fatty acids produced by *Lactobacillus apinorum* Fhon13$N^T$ were also found in the investigated honey types (Table 4).

TABLE 3

Free fatty acids, 3-OH Fas, (pmol/ml medium) in spent Pollen medium of cultivated bacteria.

| Samples | C 10:0 | C 12:0 | C 14:0 | C 16:0 |
|---|---|---|---|---|
| Blank (pollen) | — | — | — | — |
| Lactobacillus apinorum Fhon13N$^T$ | 307.9 | 252.4 | 26.7 | 51.9 |

TABLE 4

3-OH FAs (pmol/mg) in fresh honey and stored honeys.

| Sample | C 10 | C 12 | C 14 | C 16 |
|---|---|---|---|---|
| Fresh honey | 0.5 | 0.1 | | 0.2 |
| Two weeks old honey | 0.3 | 0.1 | — | — |
| One month Rapeseed | 0.7 | | — | — |
| Rapeseed | 0.4 | 0.1 | — | — |
| Linden | 0.9 | 0.3 | — | 0.9 |
| Raspberry | 0.6 | 0.2 | — | — |
| Honey dew | 0.7 | 0.2 | — | — |
| Heather | 0.5 | 0.2 | — | — |
| Manuka | 0.4 | 0.1 | — | — |

At least three of these 3-OH FAs; C10, C12 and C14 have been found to be active against yeast and the antifungal activity is connected to the detergent-like properties of the compounds that affect the cell membrane of target microorganisms. The pathogenic yeast tested in our study was *Candida albicans* where an inhibition against this wound pathogen was detected.

Example 4—2-Heptanone

The ability of the two type strains and their respective subspecies (from other honeybee species) to produce 2-Heptanone was tested (Olofsson, T. C. Butler E, Markowicz P, Lindholm C, Larsson L, Vásquez A. Lactic acid bacterial symbionts in honeybees—an unknown key to honey's antimicrobial and therapeutic activities. International Wound Journal 2016 October; 13(5):668-79).

The two strains were cultivated separately in 10 ml (15 ml tubes, Sarstedt) suppl. MRS and Pollen media (25) at 35° C. during 3 days. A viable count was performed for both LAB and their respective cfu values are displayed in table 4. Bacterial cultures were then cleaned by using 0.6 g of resin for 10 ml culture. Bacterial samples were centrifuged at 3000 rpm for 10 min, thereafter 5 ml of each sample supernatant was transferred to a 10 ml glass test tube following extraction twice with 3-ml of dichloromethane (Sigma-Aldrich, Germany) containing deuterated N-octanol (D17) (Cambridge Isotopes Laboratories, Inc. USA) as an internal standard. The bottom phase was transferred to a 1 ml GC test tube and analyzed as described below.

A Varian model 3800 gas chromatograph equipped with a combiPAL autosampler (CTC Analytics AG, Zwingen, Switzerland) and a silica capillary column (VF5 ms, 60m× 0.25 mm ID, 1 µm film thickness, Agilent Technologies) coupled to a 1200L triple quadrupole MSMS detector (Varian INC. Walnut Creek, Calif., USA) was used. Helium was used as a carrier gas at a column flow rate of 1.0 ml/min. The column temperature was programmed to rise from 50° to 230° C. at 7° C./min where it was held for 4 min. The injector temperature was 200° C., the transfer line temperature 280° C., the ion source temperature 200° C., the electron energy 70 eV, and the filament current 50 µA. 1-µl injections in the splitless mode were used.

Samples of the LAB (n=2) cultivated in pollen medium were analyzed in SCAN mode. Then, bacteria that were found to produce clearly detectable amounts of 2-heptanone were re-analyzed. Quantification of 2-heptanone from these bacteria was performed using selected-ion monitoring (SIM). A standard curve was obtained by injecting 1.5-150 pg of 2-heptanone (Sigma-Aldrich, Germany) and 240 ng of deuterated N-octanol (internal standard). The detection limit of 2-heptanone was 1 ng/ml and the extraction efficiency was 112%.

TABLE 5

Results showing 2-heptanone production by one of the two *Lactobacillus* from honeybees (*L. apinorum* Fhon13N$^T$). Studied Fhon13 subspecies originating in other bee species were *Lactobacillus* kohmto18, *Lactobacillus* nuhmto23 and *Lactobacillus* cehmto2 in triplicate.

| Sampled strains | ng/sample* | CFU |
|---|---|---|
| Quant1 | | |
| MRS blank | 11.7 | — |
| *L. apinorum* Fhon13N$^T$ (1) | 575.1 | $3.0 \times 10^7$ |
| *L. apinorum* Fhon13N$^T$ (2) | 696.3 | |
| *L. apinorum* Fhon13N$^T$ (3) | 611.7 | |
| Pollen (Cleaned blank) | 9.8 | — |
| *L. apinorum* Fhon13N$^T$ (1) | 771.3 | $3.0 \times 10^7$ |
| *L. apinorum* Fhon13N$^T$ (2) | 724.8 | |
| *L. apinorum* Fhon13N$^T$ (3) | 875.8 | |
| Pollen blank | 140.6 | — |
| *L. apinorum* Fhon13N$^T$ | 888.2 | $8.0 \times 10^8$ |
| Quant 2 | | |
| Pollen blank | 44.1 | — |
| *L. apinorum* Fhon13N$^T$ (1) | 926.5 | $1.5 \times 10^8$ |
| *L. apinorum* Fhon13N$^T$ (2) | 863.6 | |
| *L. apinorum* kohmto18 (1) | 476.9 | $4 \times 10^8$ |
| *L. apinorum* kohmto18 (2) | 501.0 | |
| *L. apinorum* kohmto18 (3) | 495.4 | |
| *L. apinorum* nuhmto23 (1) | 565.1 | $1.5 \times 10^9$ |
| *L. apinorum* nuhmto23 (2) | 507.9 | |
| *L. apinorum* nuhmto23 (3) | 523.4 | |
| *L. apinorum* cehmto2 (1) | 1172.3 | $2.5 \times 10^{10}$ |
| *L. apinorum* cehmto2 (2) | 1349.3 | |
| *L. apinorum* cehmto2 (3) | 1418.2 | |

A clear peak representing 2-heptanone (2-HE) was found in the samples of *Lactobacillus apinorum* Fhon13N$^T$. Different subspecies of *Lactobacillus apinorum* Fhon13 originating in other honeybees were therefore tested further and results are displayed in Table 5.

SIM analyses were made of *Lactobacillus apinorum* Fhon13N$^T$ and of the closely related subspecies isolated from *Apis koschevnikovi* (*Lactobacillus apinorum* Kohmto 18), *Apis nuluensis* (*Lactobacillus apinorum* Nuhmto 23), and *Apis cerana* (*Lactobacillus apinorum* Cehmto 2). The largest amount of 2-heptanone per colony forming unit (cfu) was found in the samples of *Lactobacillus apinorum* Fhon13N$^T$ cultivated in supplemented MRS medium. The amounts found in *Lactobacillus apinorum* Fhon13N$^T$ and *Lactobacillus apinorum* Kohmto18 cultivated in pollen medium were similar but approximately 14 times smaller than those found in *Lactobacillus apinorum* Fhon13N$^T$ in MRS. Samples of *Lactobacillus apinorum* Nuhmto23 and *Lactobacillus apinorum* Cehmto2 strains contained the smallest amount of 2-heptanone. Both media (suppl. MRS and Pollen) contain traces of 2-heptanone (Table 5). The pollen medium holds higher amounts of the analyzed compound that may be explained by the fact that the same LAB strains are inoculated into collected bee pollen in the production of bee bread (honeybee larval food).

2-heptanone is a known honeybee pheromone that we here, for the first time, show it is produced by one of the honeybee LAB symbionts, *Lactobacillus apinorum* Fhon13N$^T$, and all tested closely related subspecies isolated from other bees in the world (Table 5). It has recently been discovered that 2-heptonone acts as a local anesthetic that paralyze *Varroa* mites and wax moth larvae by the honeybee bite, the 2-heptanone coming from and produced in the mandibular glands of the honeybee. Our results show that 2-heptanone is actually produced by *Lactobacillus apinorum* Fhon13N$^T$ that reside in mandibular glands (perhaps temporarily) or in the vicinity of them.

In a wound application, 2-heptanone display the same function as an anesthetic, which is promising as chronic wounds cause long-term pain in patients. Furthermore the effect of 2-heptanone may be lowering of inflammation, which could enhance wound healing.

Example 5—Seasonal Cfu Numbers of
*Lactobacillus apinorum* Fhon13N$^T$

Problems with the *Varroa* mites and wax moth larvae are seasonal and most obvious in the late summer in south of Sweden. Numbers of individual LAB residing in honeybees and their processed food vary through the year due to food, weather, treatment of bees and diseases.

We wanted to investigate when the two strains *Lactobacillus apinorum* Fhon13N$^T$ and *Lactobacillus mellifer* Bin4N$^T$ are found in high numbers in honeybees and their processed foods. Twenty-seven beehives were sampled throughout one year sampling the bees and their processed foods.

Both type strains *Lactobacillus apinorum* Fhon13N$^T$ and *Lactobacillus mellifer* Bin4N$^T$ were detected in highest colony forming units (cfu) in the late summer suggesting that they are needed the most during that period of the year.

Example 6—Mead

Mead is an alcoholic beverage made from honey and water that ferment.

Mead might have been an important beverage in many cultures keeping people healthy. Our results show that it is impossible to produce mead in a traditional way from fresh honey without the bee specific lactic acid bacteria playing a central role. In current commercial mead production no bee lactic acid bacteria are present; only yeast, due to the use of ripe honey that is boiled together with water prior to mead fermentation where certain industrial yeast is inoculated.

We have produced mead with all the 13 bee specific lactic acid bacteria including both type strains *Lactobacillus apinorum* Fhon13N$^T$ and *Lactobacillus mellifer* Bin4N$^T$ together with natural yeasts from the harvested honey that naturally contains flower pollen, as honey always do.

Seven different batches of mead were produced with honey containing the said microorganisms. The result pointed out clearly that:

1. The growth of the natural yeast strains in the fermenting mead was clearly inhibited by the LAB and highly probable by free fatty acids produced by *Lactobacillus apinorum* Fhon13N$^T$. Further more individual tests showed that both strains produced PLA and OH-PLA, which are also known substances that inhibit both yeast and bacteria. The yeasts were running their metabolisms, during fermentation, producing alcohol but with suppressed results producing a healthier beverage with less alcohol content.
2. The cfu numbers of LAB after fermentation was very high, 1 billion per deciliter, which is very beneficial for a potential consumer. The high growth numbers were possible due to inhibition of yeast with metabolites from both type strains *Lactobacillus apinorum* Fhon13N$^T$ and *Lactobacillus mellifer* Bin4N$^T$ together, that otherwise would have dominated.
3. Growth rates were higher with honey and pollen as nutrients. A trial was performed testing growth rates of both type strains *Lactobacillus apinorum* Fhon13N$^T$ and *Lactobacillus mellifer* Bin4N$^T$ on commercial growth media in comparison with growth on their natural food honey and pollen. Both strains grew faster and to higher numbers with their natural food similar to the ingredients in Mead resulting in a strong ability to compete with yeasts regarding nutrition's leading to indirect inhibition of yeast growth.

The invention claimed is:

1. A method for the manufacturing of a product comprising the steps of:
    a) isolating at least one bacterial strain chosen from *Lactobacillus apinorum* Fhon13N$^T$ having deposition number LMG P-28345 and *Lactobacillus mellifer* Bin4N$^T$ having deposition number LMG P-28344 having the ability to produce benzene and/or ethylbenzene and/or free fatty acids and/or 2-heptanone from honeybees and their processed food,
    b) growing said at least one bacterial strain,
    c) mixing said bacterial strain with a salt or sugar source and
    d) obtaining a product with from about $10^1$ to $10^{14}$ CFU/g of the strains.

2. A method according to claim 1, wherein the sugar source is selected from the group consisting of honey, sugar, fructose, sucrose, dextrine, maltose, and glucose.

3. A method according to claim 2, wherein the sugar source is honey.

* * * * *